US008437731B2

(12) United States Patent
Reich et al.

(10) Patent No.: US 8,437,731 B2
(45) Date of Patent: May 7, 2013

(54) EMERGENCY CALL ANALYSIS SYSTEM

(76) Inventors: Don Reich, Thousand Oaks, CA (US); Kurt Warner, Ventura, CA (US)

( * ) Notice: Subject to any disclaimer, the term of this patent is extended or adjusted under 35 U.S.C. 154(b) by 89 days.

(21) Appl. No.: 13/016,729

(22) Filed: Jan. 28, 2011

(65) Prior Publication Data

US 2012/0196557 A1    Aug. 2, 2012

(51) Int. Cl.
*H04M 11/04* (2006.01)

(52) U.S. Cl.
USPC ............. 455/404.1; 455/404.2; 455/420; 455/422.1; 706/46; 706/52; 706/54

(58) Field of Classification Search .... 455/404.1–404.2, 455/422.1, 420; 706/46, 52–54
See application file for complete search history.

(56) References Cited

U.S. PATENT DOCUMENTS

| | | | |
|---|---|---|---|
| 7,269,454 B2 * | 9/2007 | Sherman ............... | 600/515 |
| 2011/0111728 A1 * | 5/2011 | Ferguson et al. ......... | 455/404.2 |

* cited by examiner

Primary Examiner — Kiet Doan
Assistant Examiner — Michael T Vu
(74) Attorney, Agent, or Firm — Brinks Hofer Gilson & Lione

(57) ABSTRACT

A method for predicting a survival rate among individuals, where the survival rate depends in part on a responsiveness of emergency personnel, and the responsiveness of the emergency personnel depends in part on an amount of time taken to route an emergency call to a primary emergency response center, includes determining, by a computer system, a number of emergency calls initially routed to a primary emergency response center. The computer system determines a number of emergency calls initially routed to a secondary emergency response center that, in turn, routes the emergency calls to the primary emergency response center. The computer system calculates a survival rate amount individuals according to a function of the determined number of the number of emergency calls initially routed to a primary emergency response center and the number of emergency calls initially routed to a secondary emergency response center. The calculated survival rate is displayed on a terminal.

20 Claims, 11 Drawing Sheets

320

06:03:11 CONSOLE 4041 OPERATOR MORRIS, V RD READY
------------------------------------------------------------
(209) 468-4595 MI009 06:02:01 I RI 06:02:07 I CO007 06:02:10 I A6711 06:02:10
I DI007 06:03:03 I RLS 06:03:03 I DUR 00:01:02
2010/04/01
200 (209) 468-4595 ALI NOT ALLOWED
06:02:18 CONSOLE 1706 OPERATOR SCOTT, M READY
------------------------------------------------------------
------------------------------------------------------------
(209) 468-6591 MI004 06:00:14 I RI 06:00:20 I CO002 06:00:22 I A7373 06:00:22
I DI002 06:03:04 I RLS 06:03:05 I DUR 00:02:51
2010/04/01
200 (209) 468-6591 ALI NOT ALLOWED
------------------------------------------------------------
(800) 470-1000 MI005 06:02:25 I RI 06:02:31 I CO003 06:02:33 I A0027 06:02:33
INBOUND PBX #1 05:57:28
I DI003 06:03:06 I RLS 06:03:06 I DUR 00:00:41
I RCVD 3113 05:57:31 I ANSW 3113 05:57:32 I THLD 3113 05:58:47
( ) OUT-CALL MI008 06:02:38 I CO004 06:02:38 I DI004 06:03:57 I RLS 06:03:58
2010/04/01
I DUR 00:01:20
2010/04/01
12102477503
200 (800) 470-1000 ALI NOT ALLOWED
------------------------------------------------------------

Fig. 3B

EMERGENCY CALL ANALYSIS SYSTEM

BACKGROUND

Emergency calls originating from landline and cellular phones are configured to be automatically routed to public safety answering points (PSAP). Each emergency call may include information that enables determining a location of the caller, and the number of the caller. In the case of cellular phones, carrier information may be provided.

The PSAP may correspond to a primary emergency response center capable of coordinating an emergency response, such as a local police department in a town. PSAPs may also correspond to secondary emergency response centers, such as state highway patrol departments. In some instance, these PSAPs may not be prepared to coordinate an emergency response. Rather, the secondary emergency response center may route an emergency call to a primary response center.

A PSAP responding to an emergency call may gather additional information associated with the emergency call, such as the amount of time the caller waited for personnel to answer the call, a number of rings, whether the caller abandoned the call. Other information, such as whether the call was transferred to a primary emergency response center, may be gathered.

One problem with this arrangement, however, is that the information from the various PSAPs is not consistent between PSAPs, which makes determining trends associated with emergency calls difficult. Moreover, no common method for gaining access to the information exists. Therefore, determining emergency call information at, for example, a statewide level is difficult, if not impossible.

As noted above, a cellular telephone tower may or may not be routed to primary response centers. In many instances, a cellular tower is configured to route emergency calls to a secondary emergency response center. In other cases, the cellular tower is configured according to empirical data that indicates an optimal primary emergency response center that will more effectively serve as a PSAP for emergency calls communicated via the cellular tower. Cellular towers routed based on empirical data to primary emergency response centers are hereinafter referred to as RED sectors as they are routed based on empirical data.

In emergency situations where every second counts, the configuration of a cellular tower can mean the difference between life and death. For example, it is well established that an individual suffering from a cardiac arrest only has about six minutes to survive. As such, the survival rate of such an individual depends in part on a responsiveness of emergency personnel. The responsiveness of emergency personnel in part turns on an amount of time taken to route an emergency call to a primary emergency response center. Emergency calls routed through non-RED sector cellular towers (i.e., cellular towers routed to secondary emergency centers) will take longer to reach appropriate emergency personnel than those routed through RED sector-type cellular towers.

BRIEF SUMMARY

Methods, system, and computer-readable media are provided for communicating information associated with emergency calls communicated to emergency response centers.

In a first aspect, a method for communicating information associated with emergency calls communicated to emergency response centers may include receiving, by an emergency call analysis system, emergency call information that defines an emergency call communicated to an emergency response center within a geographic region. The emergency call information includes location information of the emergency call. The emergency call analysis system may determine statistical information associated with emergency calls made within a geographic region. A computer server may then generate browser code executable by a browser to cause the browser to display the statistical information.

In a second aspect, a system is provided for communicating information associated with emergency calls communicated to emergency response centers. The system includes an emergency call analysis system configured to receive emergency call information that defines an emergency call communicated to an emergency response center within a geographic region. The emergency call information includes location information of the emergency call. The emergency call analysis system is also configured to determine statistical information associated with emergency calls made within a geographic region. A computer server is configured to generate browser code executable by a browser to cause the browser to display the statistical information.

In a third aspect, a non-transitory computer-readable storage medium is provided. The storage medium includes instructions for receiving emergency call information that defines an emergency call communicated to an emergency response center within a geographic region. The emergency call information includes location information of the emergency call. Instructions are provided for determining statistical information associated with emergency calls made within a geographic region and generating browser code executable by a browser to cause the browser to display the statistical information.

In a fourth aspect, a method for predicting a survival rate among individuals, where the survival rate depends in part on a responsiveness of emergency personnel, and the responsiveness of the emergency personnel depends in part on an amount of time taken to route an emergency call to a primary emergency response center, includes determining, by a computer system, a number of emergency calls initially routed to a primary emergency response center. The computer system determines a number of emergency calls initially routed to a secondary emergency response center that, in turn, routes the emergency calls to the primary emergency response center. The computer system calculates a survival rate amount individuals according to a function of the determined number of the number of emergency calls initially routed to a primary emergency response center and the number of emergency calls initially routed to a secondary emergency response center. The calculated survival rate is displayed on a terminal.

In a fifth aspect, a system for predicting a survival rate among individuals, where the survival rate depends in part on a responsiveness of emergency personnel, and the responsiveness of the emergency personnel depends in part on an amount of time taken to route an emergency call to a primary emergency response center, includes a computer system configured to determine a number of emergency calls initially routed to a primary emergency response center and a number of emergency calls initially routed to a secondary emergency response center that, in turn, routes the emergency calls to the primary emergency response center, and calculate a survival rate amount individuals according to a function of the determined number of the number of emergency calls initially routed to a primary emergency response center and the number of emergency calls initially routed to a secondary emergency response center. A server is configured to generate browser code executable by a browser to cause the browser to display the calculated survival rate on a terminal.

In a sixth aspect, a non-transitory machine-readable storage medium is provided. The non-transitory machine-readable storage medium stores includes at least one code section for determining a number of emergency calls initially routed to a primary emergency response center, determining a number of emergency calls initially routed to a secondary emergency response center that, in turn, routes the emergency calls to the primary emergency response center, and calculating a survival rate amount individuals according to a function of the determined number of the number of emergency calls initially routed to a primary emergency response center and the number of emergency calls initially routed to a secondary emergency response center.

The present invention is defined by the following claims, and nothing in this section should be taken as a limitation on those claims. Further aspects and advantages of the invention are discussed below in conjunction with the preferred embodiments.

DETAILED DESCRIPTION

Embodiments below describe an exemplary system configured to process information from emergency calls to determine statistical information about the nature of the emergency calls. The system is configured to generate a group of webpages, hereinafter referred to as dashboards, to convey the statistical information. The dashboards are viewable via a computer browser.

The dashboards are configured to maximize an amount of information displayed. The dashboards display a geographic region that enables locating the source of an emergency call. The dashboards further display sub regions of the geographic region. Statistical information may be broken down according to sub regions and displayed on the dashboards.

Other embodiments are provided for generating a dashboard configured to enable an operator to predict a number of lives that may be saved during a medical emergency, such as a cardiac arrest. The dashboards are configured to generate a prediction of the number of lives saved based in part on whether a cellular tower is routed to a primary emergency response center or a secondary emergency response center.

Figure 1:
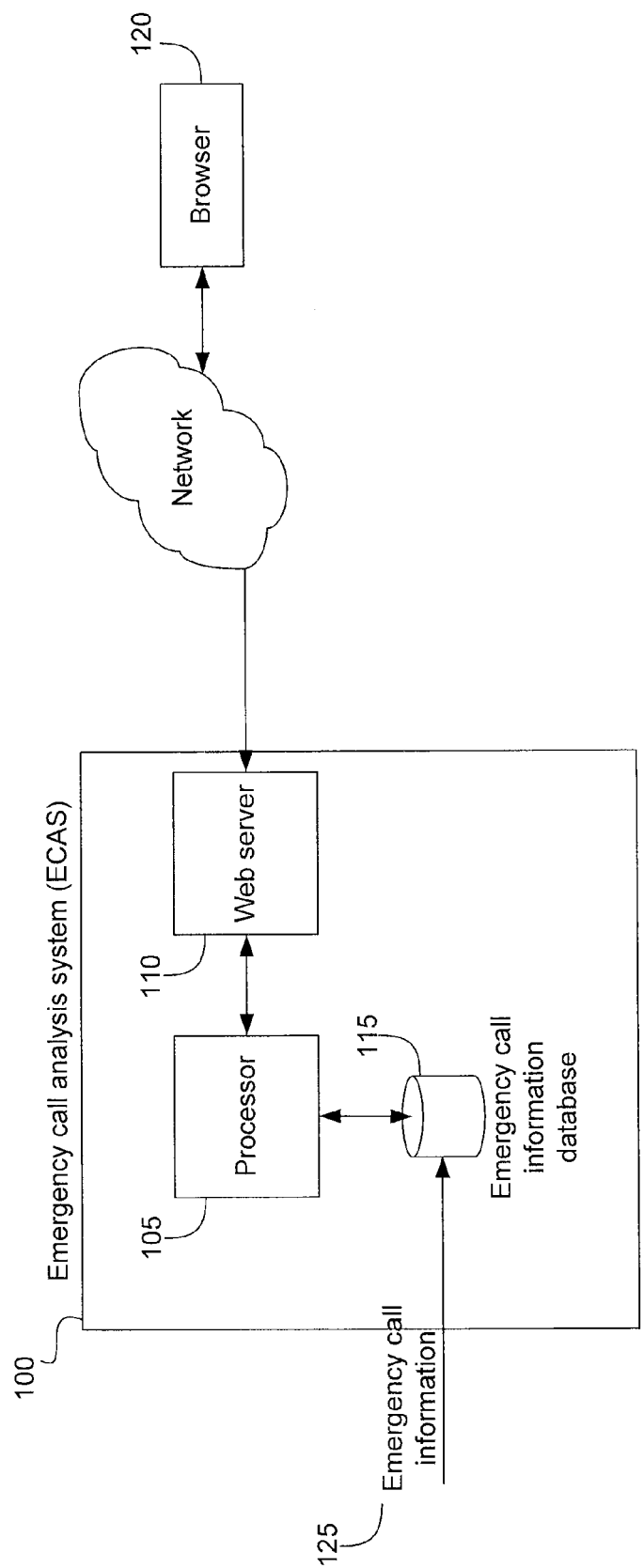
FIG. 1 is an exemplary emergency call analysis system (ECAS)

FIG. 1 is an exemplary emergency call analysis system (ECAS) 100. The ECAS includes a processor 105 and a web server 110. Also shown are an emergency call database 115 and a browser 120 in communication with the ECAS 100.

The processor 105 and web server 110 may correspond to an Intel®, AMD®, or PowerPC® based computer or a different computer. The processor 105 and web server 110 may include an operating system, such as a Microsoft Windows®, Linux, or other Unix® based operating system. The processor 105 and web server 110 may be implemented within a single computer system or be separate. The processor 105 and web server 110 may be configured to communicate with other computers via an interface, such as a network interface.

The processor 105 is configured to analyze emergency call information 125 communicated by any number of networks or databases that provide emergency call information associated with wired and wireless phones. For example, the emergency call information 125 may be communicated from a PSAP, a PSAP controller, or other source via a network. The emergency call information may include Automatic Number Identification (ANI) information for determining a number of the caller, Automatic Location Identification Information (ALI) that enables determining a geographic location of a user initiating an emergency call, a number of the caller, the emergency response center (e.g., PSAP) to which the call was routed, how many rings occurred before the call was answered, whether the call was transferred from a secondary emergency response center to a primary emergency response center, whether the call was abandoned, and/or a reason for the call. Other information may be included in the emergency call information 125.

Exemplary systems configured to gather emergency call information from a variety of sources that may be used in connection with the embodiments disclosed herein are described in U.S. application Ser. Nos. 12/574,664, filed Oct. 6, 2009, 12/699,727, filed Feb. 3, 2010, 10/791,954, filed Mar. 2, 2004, 10/722,677, filed Nov. 24, 2003 (now abandoned), 09/967,291, filed Sep. 27, 2001 (issued as U.S. Pat. No. 6,775,356), 09/712,655, filed Nov. 13, 2000 (issued as U.S. Pat. No. 6,504,909), and 09/467,641, filed Dec. 20, 1999 (issued as U.S. Pat. No. 6,151,385), the contents of which are hereby incorporated by reference. Information communicated and/or processed by these systems may be stored in a single database 115 or a group of databases.

The processor 105 may analyze the emergency call information stored in the database 115 to generate statistical information associated with emergency calls. The processor 105 may generate browser executable code, such as HTML code, Java, VBScript, and/or other code, operable to display a web page that includes the statistical information. The browser code is communicated to a web server 110, which enables access to the statistical information via a network, such as the Internet.

FIGS. 2A-5 illustrates exemplary dashboards or web pages that may be generated by the processor 105 and/or web server 110 and communicated to a browser 120 via the web server 110. In this regard, the processor 105 may be configured to execute instructions stored in one or more non-transitory computer-readable media that are configured to cause the processor 105 to perform any of the operations described herein.

Figure 2A:
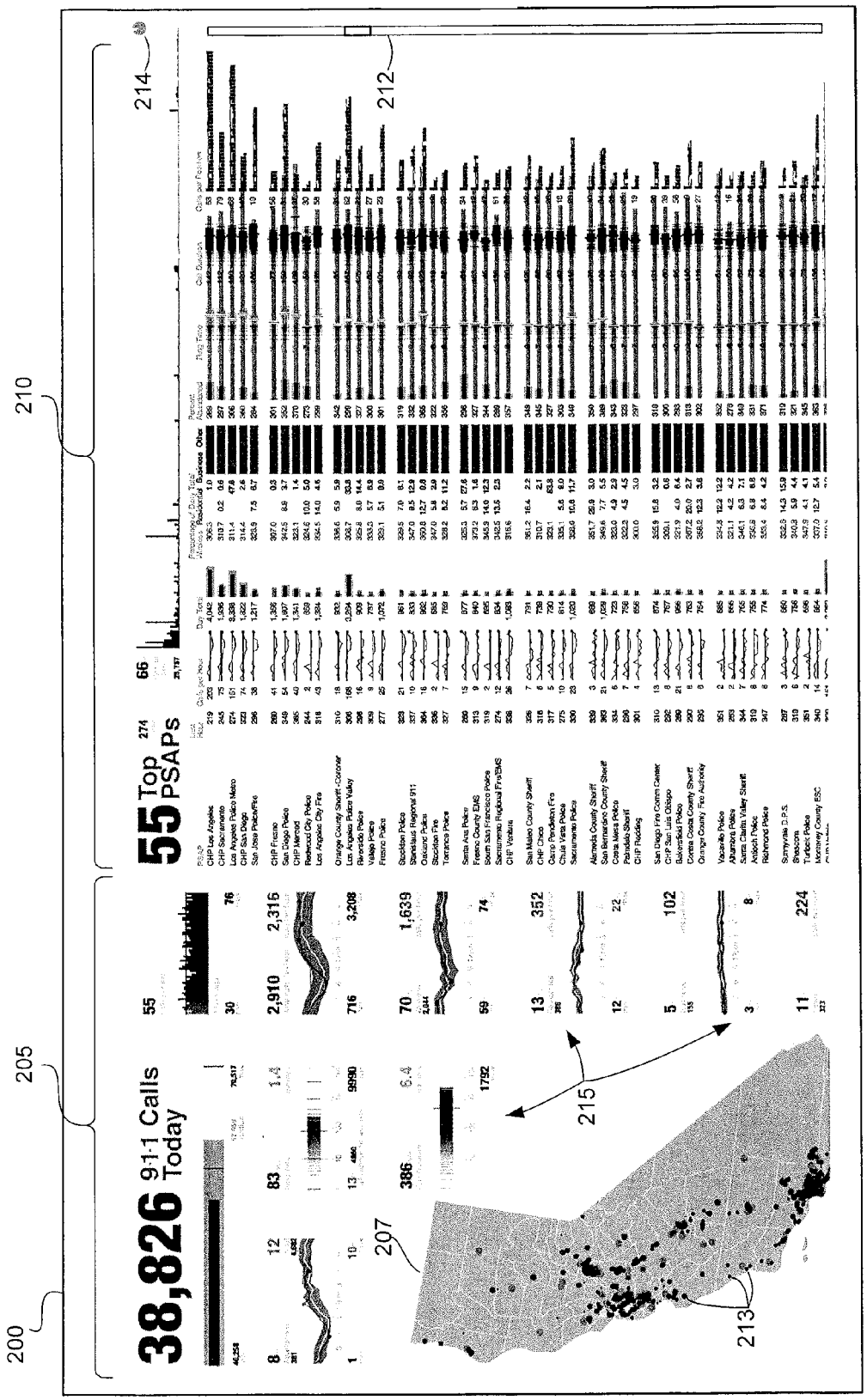
FIGS. 2A-4 are exemplary dashboards that convey statistical information associated with emergency calls that may be communicated to a user via a browser.
Figure 2B:
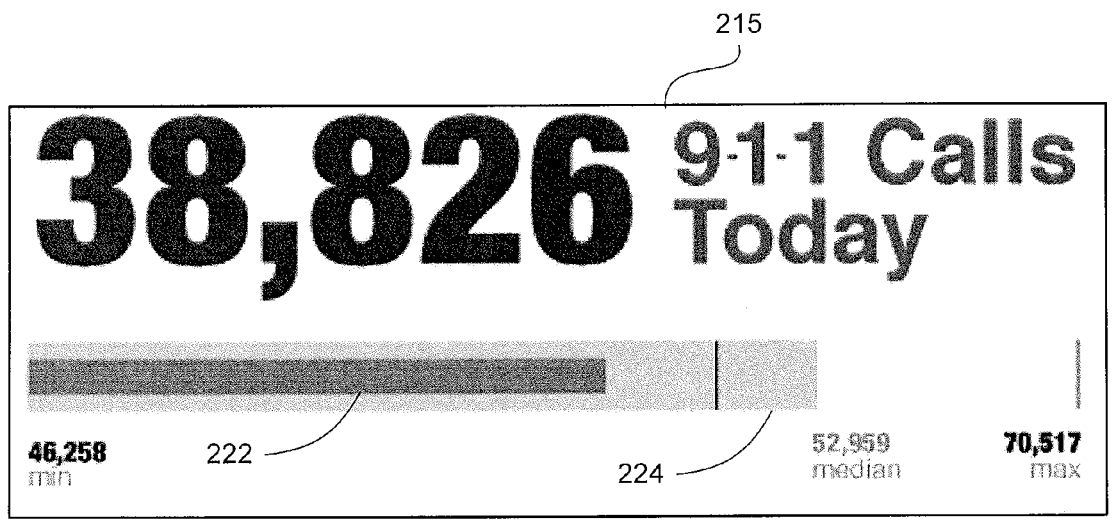

Referring to FIG. 2A, the processor 105 and/or web server may generate browser code operable to cause a browser 120 to display a first exemplary dashboard 200 configured to display information associated with emergency calls, such as 9-1-1 calls. The emergency calls for which the information is presented may correspond to all emergency calls within a geographic region 207, such as a county, state, country, continent, or other geographic region. The geographic region 207 illustrated in this case is the state of California. The same information may be provided for sub regions of the geographic region 207. The sub regions may correspond to cities, counties and the like, and/or may correspond to regions served by a given public safety answering point (PSAP).

The dashboard 200 may be divided into first and second regions 205 and 210. The first region 205 may display statistical information for emergency calls that occur within a geographic region 207, such as the state of California. The geographic region 207 within which the calls occur may also be shown. An indication of the location of a PSAP to which the emergency call is routed may be superimposed on the geographic region 207. For example, a location symbol 213, such as a colored dot, may be shown to represent the location of the PSAP. The color, intensity, and/or size of the symbol 213 may be adjusted to represent a number of calls that occur within the geographic region 207. For example, the processor 105 may determine a number of calls originating from each sub region of the geographic region 207 and configure the symbol accordingly (e.g., change the color intensity) to indicate the relative number of emergency calls from each sub region. Alternatively or in addition, the location of the caller that originated the emergency call may be superimposed on the geographic image 207 and indicated as described above.

The second region 210 may display statistical information associated with various sub regions of the geographic region 207, such as counties, municipalities, etc., and/or by PSAP. To save display real estate, the number of sub regions listed may be limited. For example, the actual number of sub regions may be around 450. However, it may not be possible to display such a high number of sub regions within a given display. Therefore, the sub region list may be restricted to a subset number of sub regions. For example, statistical information associated with the top 55 PSAPs may be displayed in the second region 210. The top 55 PSAPs may correspond to those PSAPs that receive the highest call volume. The sub regions may be sorted based on call volume or a different metric. In some implementations, a scroll bar 212 is provided to enable scrolling through second region 210 to display other PSAPs. Other implementations may enable zooming the second region in and out to enable viewing a greater or lesser number of sub regions.

Information shown in the dashboard 200 may be periodically updated, such as every minute, hour, or at a different interval. For example, the processor 105 may generate code that implements a timer in the browser code that is configured to cause the browser to periodically request updated information from the ECAS 110. In this regard, browser code may be configured to display a timer symbol 214 that indicates the amount of time until a next automatic update.

In the first region 205, statistical information associated with emergency calls is broken into several statistical elements, each of which is visually represented via a visual element 215, such as a chart. The various visual elements 215 of the control dashboard are shown in FIGS. 2B-2J for clarity. Each visual element 215 may include a minimum, median and maximum number associated with a statistical element. Each visual element 215 may display a running prediction of the value represented by the visual element. The prediction may be determined by averaging a given value over a period, such as one day, week, month, etc. An average value for different times of the day may be determined, such as a minute-by-minute average or an hour-by-hour average. Minimum and maximum values over the period and throughout a day may be determined. The processor 105 may compute the various values for each statistical element. Once computed, the processor 105 embeds the respective values within the browser code so that the values are displayed when the dashboard 200 is presented. In other implementations, the processor 105 generates browser code, executed by the browser that is configured to determine the respective values described above.

The visual elements 215 may include color information to enable the conveyance of additional information. For example, referring to FIG. 2B, a first visual element 215 may indicate the current number of calls received in a first color 222 (e.g., blue) and a run-rate prediction of the number of calls that will be received in a second color 224 (e.g., grey). A third color (e.g., red) may be utilized to represent the case where a current value exceeds a maximum threshold for that statistical element. For example, if the current number of calls shown in first visual element 220 were to exceed a maximum threshold, the color used to indicate the current number of calls may be changed from blue to red to draw the attention of an operator to the possibility that there may be a problem. For example, the occurrence of large-scale emergency may trigger a ten- or hundred-fold increase in the number of emergency calls to PSAPs. The number of calls may exceed typical maximums and, therefore, be shown in red.

Figure 2C:
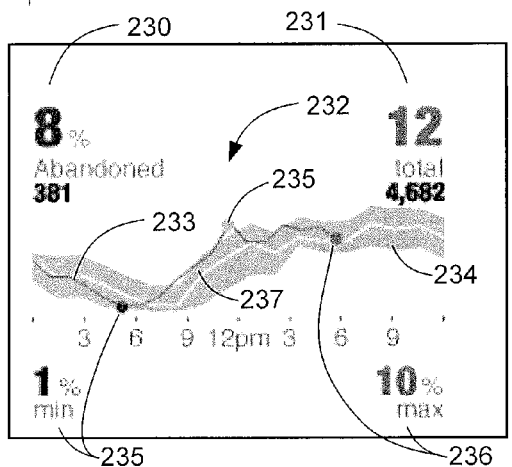
Figure 2D:
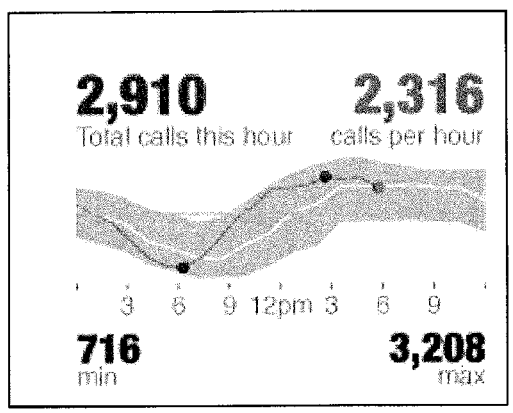
Figure 2E:
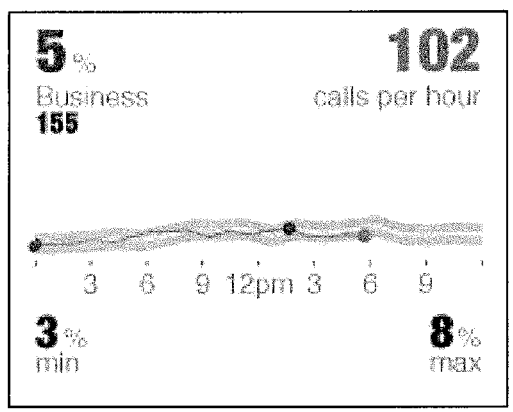
Figure 2F:
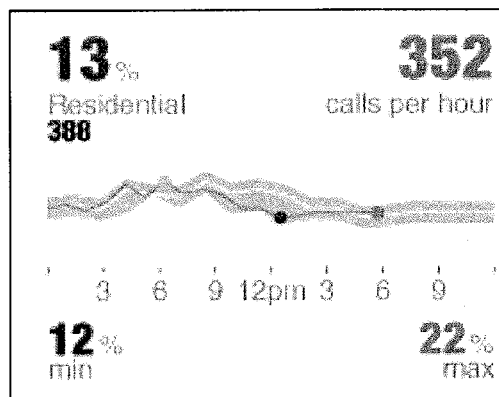
Figure 2G:
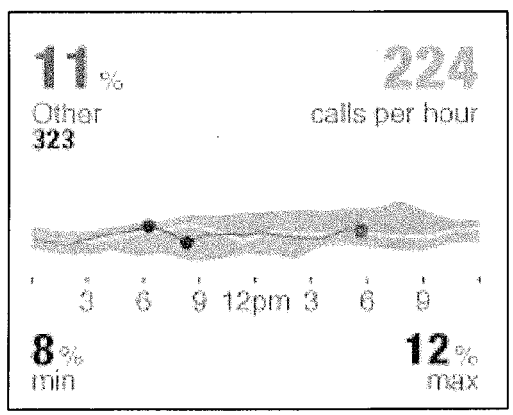
Figure 2H:
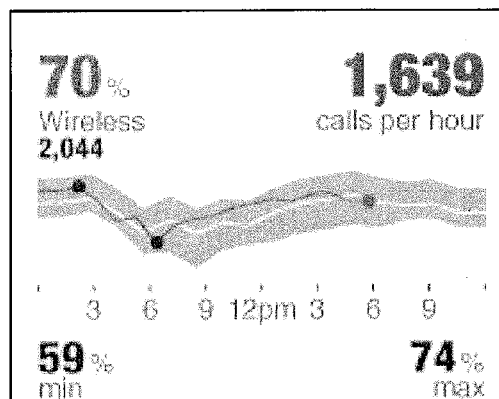

FIGS. 2C and 2D illustrate visual elements 215 that display information associated with abandoned calls and total calls, respectively. FIGS. 2E-2H respectively illustrate visual elements 215 that display information associated with a number of business, residential, wireless calls, and other calls that cannot be classified as one of the three. For example, referring to FIG. 2c, a current percentage and number of abandoned calls 230 may be shown along with a predicted percentage and number of abandoned calls 231. The predicted number of abandoned calls may correspond to an average number of abandoned calls that occurred over a period. A current value line 233 on the graph 232 corresponds to the current number of abandoned calls that occurred during a day. A prediction line 234 graphs the predicted number of abandoned calls at a given time of day. The upper and lower bounds of the prediction line 234 represent the average maximum and minimum values, respectively, throughout the day. A centerline 237 represents the average value throughout the day. Any deviation in the current value line above the upper bound of the prediction line 234 maximum threshold may be emphasized. For example, a deviating point 235 may be illustrated in red. A minimum percentage 235 and maximum percentage 236 of abandoned calls experienced during the measurement may also be displayed in the visual element.

The visual elements shown in FIGS. 2D-2H convey similar types of statistical information albeit associated with the information represented by the respective visual elements. Thus, the visual elements 215 are configured to convey a maximum amount of information within a relatively small display space. This in turn enables placement of many visual elements to convey a large amount of information on a single display.

Figure 2I:
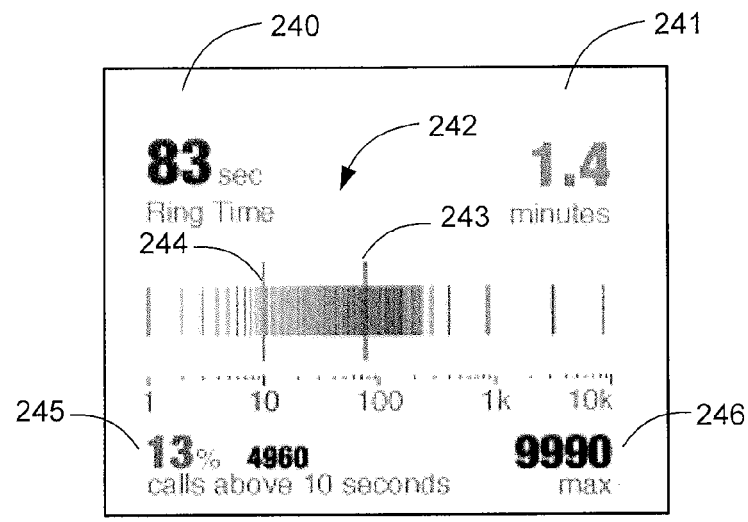
Figure 2J:
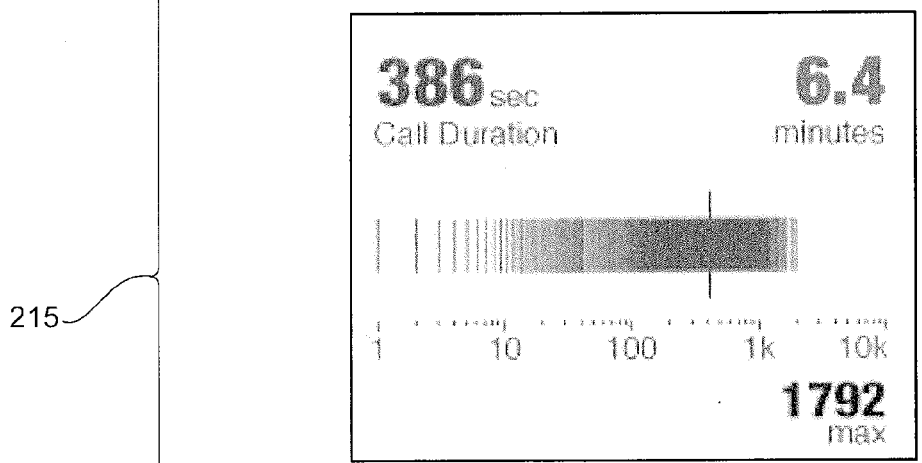

FIGS. 2I and 2J are visual elements 215 that display information associated with ring times and call durations, respectively. For brevity, aspects of the visual elements are described with reference to FIG. 2I. However, it should be understood that the visual elements of FIG. 2J convey similar information with respect to call durations. Referring to FIG. 2I, a current ring time 240 is displayed. The current ring time 240 corresponds to the ring time of a current call. A predicted average ring 241 is also shown. A graph 242 displays the ring times of emergency calls generated within, for example, a one-hour time period. A first indicator displayed on the graph 242 represents the current ring time 243. A second indicator on the graph 243 represents a maximum ring time threshold 244. The maximum ring time threshold 244 may be computed by the processor 105 and may correspond to an average ring experienced during a period such as a day, week, year or other period. Alternatively, an operator may specify the maximum ring time threshold 244. The percentage and number of calls 245 that exceed the maximum ring time threshold 244 may be displayed. A predicted maximum number of calls 246 that exceed the maximum ring time threshold 244 may also be displayed.

Figure 2K:
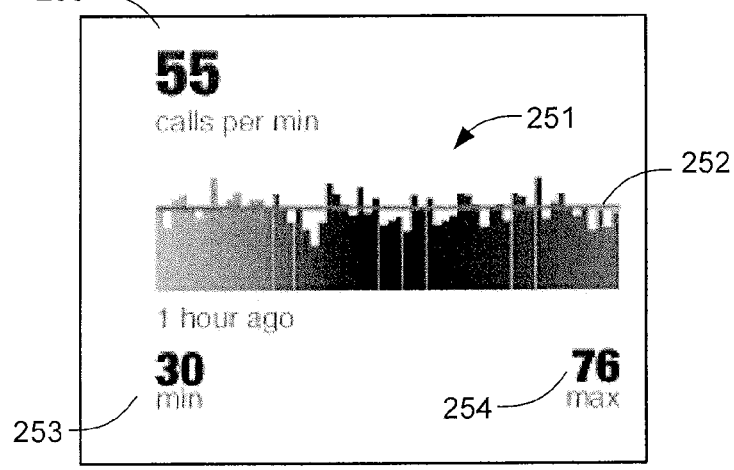

FIG. 2K illustrates a visual element 215 that displays calls-per-minute information. The visual element 215 displays the current number of calls per minute 250. A graph 251 displays the number of calls per minute received over a period, such as one hour. Minimum and maximum number of calls-per-minute threshold statistics 253 and 254 are displayed. A calls-per-minute threshold value 252 is displayed. The processor 105 may calculate the calls-per-minute threshold value 252. For example, the processor 105 may compute an average number of calls per minute 252 received over a period, such as a year, month, week, etc., to obtain the calls-per-minute threshold value 252. Alternatively, an operator may specify the calls-per-minute threshold value 252. In some implementations, the color of the number of calls per minute 250 and/or the other displayed numbers and elements may be changed when the actual number of calls per minute 252 exceeds the calls-per-minute threshold value 252.

Figure 2L:
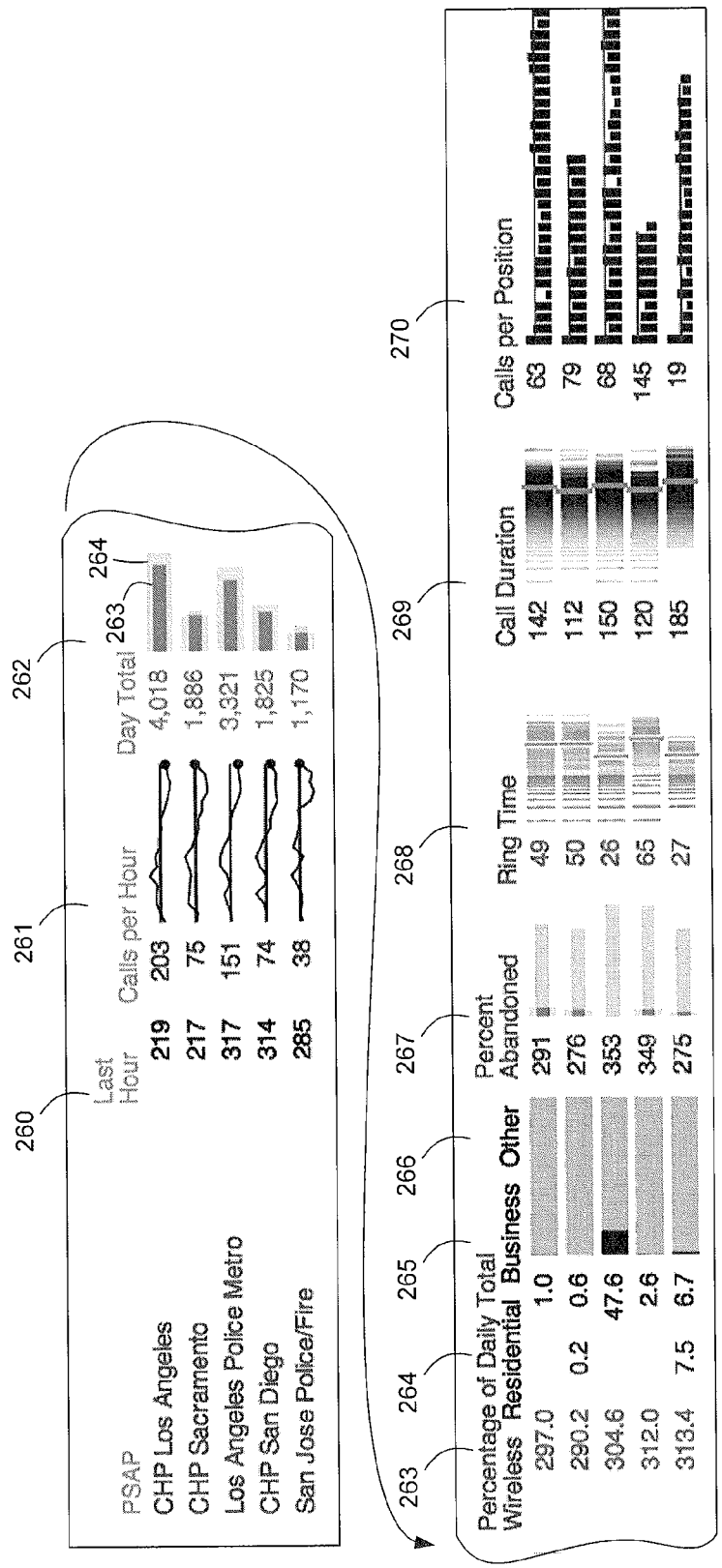

FIG. 2L illustrates a portion of the statistical information associated with the subset regions displayed in the second region 210. In this case, the subset regions correspond to PSAPs of the state of California. Statistical information for each PSAP is represented in a group of columns identified by headings labeled last hour 260, calls-per-hour 261, and day total 262.

The last hour column 260 indicates the number of emergency calls received by a PSAP in the last hour. The calls-per-hour column 261 displays a number and a graph. The number corresponds to the maximum number of calls a PSAP can handle. The maximum number may be based on a historical maximum number of calls the PSAP has received. The graph displays the number of calls received in a given hour. However, other periods may be represented. (E.g., a day, a week, a month, etc.) The maximum number of calls the PSAP can handle is represented as a horizontal line on the graph.

The day total column 262 displays a number that correspond to the total number of calls received by the PSAP in the current day, and a bar graph displays the total number of calls 263 superimposed over a predicted call volume 264 to enable quickly ascertaining whether the number of calls is about to exceed or exceeds the predicted call volume 264. As described above, the graph and/or other numbers described may be configured to change color when a maximum predicted value is exceeded. For example, the processor 105 may generate browser code configured to change the color of a given display element when the predicted value is exceeded. This advantageously alerts an operator of the condition.

Other columns indicate the percentage of wireless 263, residential 264, business 265, and other calls 266, as described above. A percentage of abandoned calls column 267 displays a number of abandoned calls and a graph that is configured to indicate when the number of abandoned calls exceeds a threshold. For example, the graph may change to red to alert an operator of a high rate of abandoned calls.

A ring time column 268 and call duration column 269 indicate the average ring time and call durations associated with emergency calls to a PSAP. The ring times and call durations may be configured to indicate whether a maximum threshold has been exceeded. For example, the ring times and call durations may be displayed in red to indicate that the respective values are out of an acceptable range and may be displayed in blue to indicate that the respective values are within the acceptable range.

A calls-per-position column 270 displays a number and graph that represent the number of calls per position. A calls-per-position column 270 displays a number and graph that represent the number of calls per position or number of call takers available to receive emergency calls at a given PSAP or sub region and a relative number of emergency calls that those call takers are receiving. For example, a large PSAP, such as Los Angeles may have a large number of call takers while a smaller town may only have one or two call takers. The calls-per-position column 270 enables an operator to determine whether redistribution of the emergency call numbers is warranted. For example, geographically adjacent PSAPs may both be able to handle emergency calls from a given region. However, based on information in the dashboard 200, it may be determined that one of the PSAPs is operating at capacity as compared to the other. Therefore, a decision to reroute emergency calls to the other PSAP that has more capacity may be made.

As shown, the dashboard 200 enables an operator to quickly ascertain information associated with emergency calls communicated to PSAPs within a geographic region 207. Placing an indicator on the geographic region 207 enables quickly determining where emergency calls are occurring. The various visual elements enable an operator to determine whether any unusual conditions exist by displaying the statistical parameters associated with the emergency calls. Changing the color of various elements of the visual elements enables the operator to quickly zero-in on problem areas as they occur. Presentation of the statistical information associated with sub regions of the geographic region 207 further enables the operator to identify trouble spots.

Figure 3A:
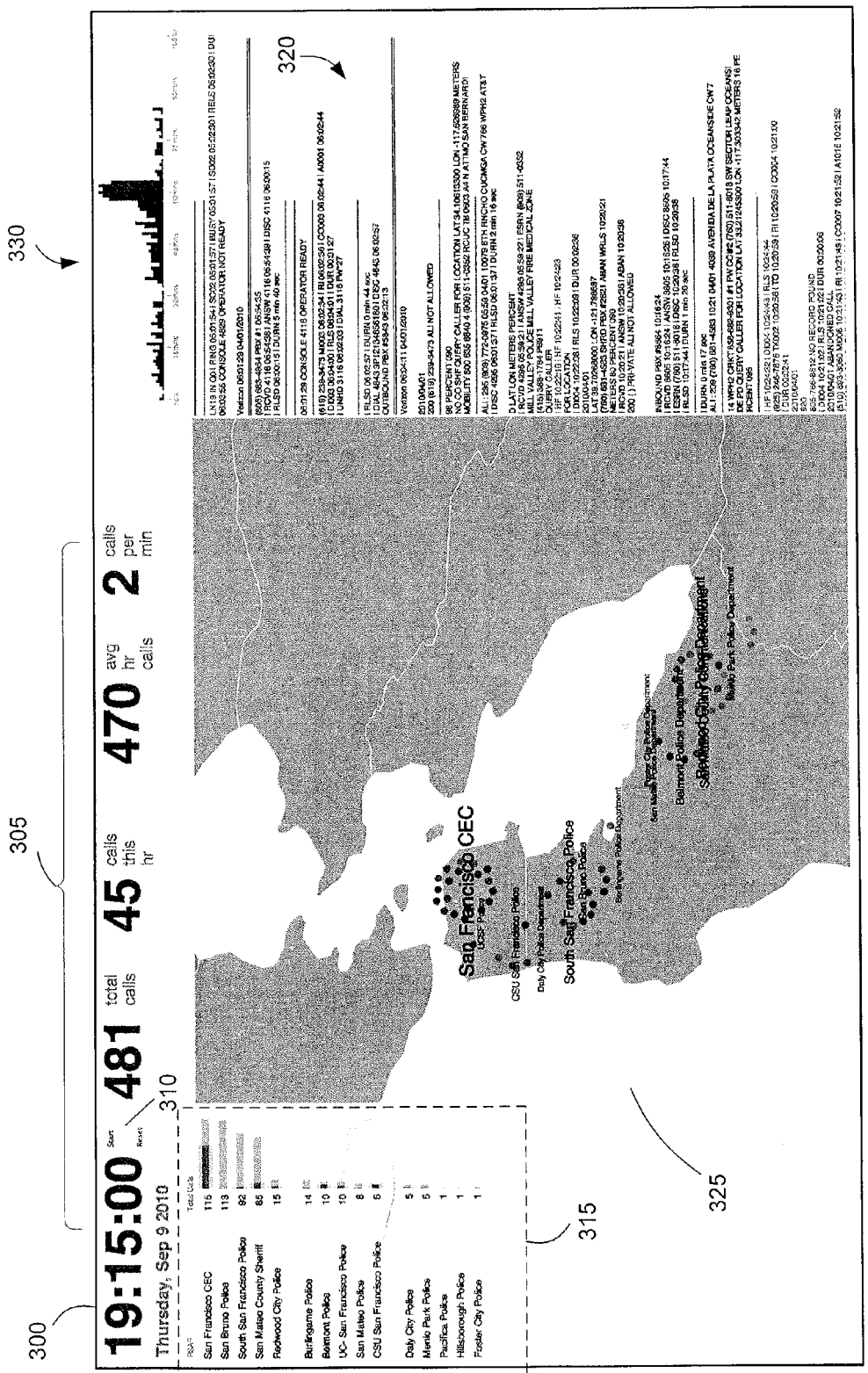

FIG. 3A illustrates a second exemplary dashboard 300 that may be communicated to a browser 120. The dashboard 300 is configured to display a location associated with emergency calls and identification information of the emergency calls in real-time. That is, the information is displayed generally within a short time of the occurrence of the emergency call. For example, the processor 105 may analyze and process the emergency call information 125 to identify information suitable for display on the dashboard 300. The processor 105 may determine whether a given emergency call occurred in the geographic region 325 displayed on the dashboard 300. If so, that emergency call may be processed and information associated with the emergency call may be displayed in real-time on the dashboard 300.

The dashboard 300 includes a geographic region 325, call volume information region 315, and identification information 320. The dashboard 300 also displays a status region 305 that includes a timestamp, a total number of calls, a number of calls per hour, an average number of calls per hour, and an average number of calls per minute. A chart 330 displays the number of calls per minute. Other status information may be provided.

As emergency calls occur, identification information 320 associated with each emergency call is scrolled within the dashboard 300. Exemplary information that may be displayed is shown in FIG. 3B. The identification information 320 for each emergency call may include a timestamp that indicates a time at which the emergency call was placed and location information. Other information, such as a network carrier through which the emergency call was routed, may be displayed. Additionally, information that identifies the PSAP to which the emergency call was routed may be displayed. Other information may be displayed as well.

In some implementations, a location symbol may be displayed on the geographic region 325 to indicate a location associated with an emergency call. As described above, the location symbol may be configured to graphically represent a number of calls occurring at a given location. The corresponding location symbols and identification information may be color-coded to enable determining identification information associated with a specific location.

The dashboard 300 enables, for example, determination of the location of the epicenter of an event, such as an earthquake. Analysis of the emergency call information may enable determining a number of regions where the earthquake was felt. This in turn may enable more efficient dispatching of emergency personnel to the affected areas.

In some implementations, the dashboard 300 may be adapted to convey historical emergency call information stored in a database 115. For example, the processor 105 may search the database 115 for emergency calls that occurred within a specified time range. A timestamp of each emergency call enables determination of a time at which the emergency called occurred.

An operator may then play back the historical information by selecting a start input field 310. The dashboard 300 may then begin to display the historical emergency call information as though it is just occurring. The historical emergency call information may be embedded in the browser code of the dashboard. Alternatively, the dashboard 300 browser code may be configured by the processor 105 to stream the historical emergency call information and/or processed information associated with the historical emergency call information from the ECAS 100.

During play back, the status region 305 may be updated to show a current total number of calls, calls per hour, average number of calls, and calls per minute. The chart 330 may be updated to show a number of calls received during a period. In addition, respective call volumes associated with different sub regions of the geographic region 325 may be reflected in the call volume information region 315. For example, the number of calls received at various PSAPs that operate in the geographic region 325 may be displayed via a bar graph. As described above, various indicator colors may be applied to the graphs to illustrate a current call volume, a predicted call volume, and whether the current call volume exceeds the predicted call volume.

By monitoring the play back of the historical call information, an operator can assess the way in which individuals respond to an actual emergency. For example, during an initial period, the emergency call volume may correspond to a baseline emergency call volume. By observing the change in the number of emergency calls and the location at which the emergency calls originate, an operator can determine where the emergency was perceived and possibly by how many individuals.

Another benefit provided by the dashboard 300 is that, in some cases, the call capacity of cellular towers within a given region may be determined. For example, the number of callers that may be "camped" on a cellular tower is finite. When the number of callers exceeds this number, new callers may receive a busy signal. However, in 911 implementations, when such a condition exists, the caller may be handed over to a different cellular tower that is within range of the caller and that has capacity. This handing over may be observed via the dashboard 300 when large numbers of emergency calls arrive at the same approximate time. For example, an emergency may be known to have occurred in a given location. However, observation of the dashboard 300 may indicate that PSAPs that are quite remote from the emergency are receiving unusually high numbers of calls. This may indicate to an operator that the call capacity of cellular towers near the emergency are saturated with callers. This in turn enables one to determine the maximum capacity of those cellular towers. This information could, for example, be beneficial to carriers that compete against one another, as a given carrier may not otherwise have knowledge of the call capacity capabilities of his competitors.

Figure 4:
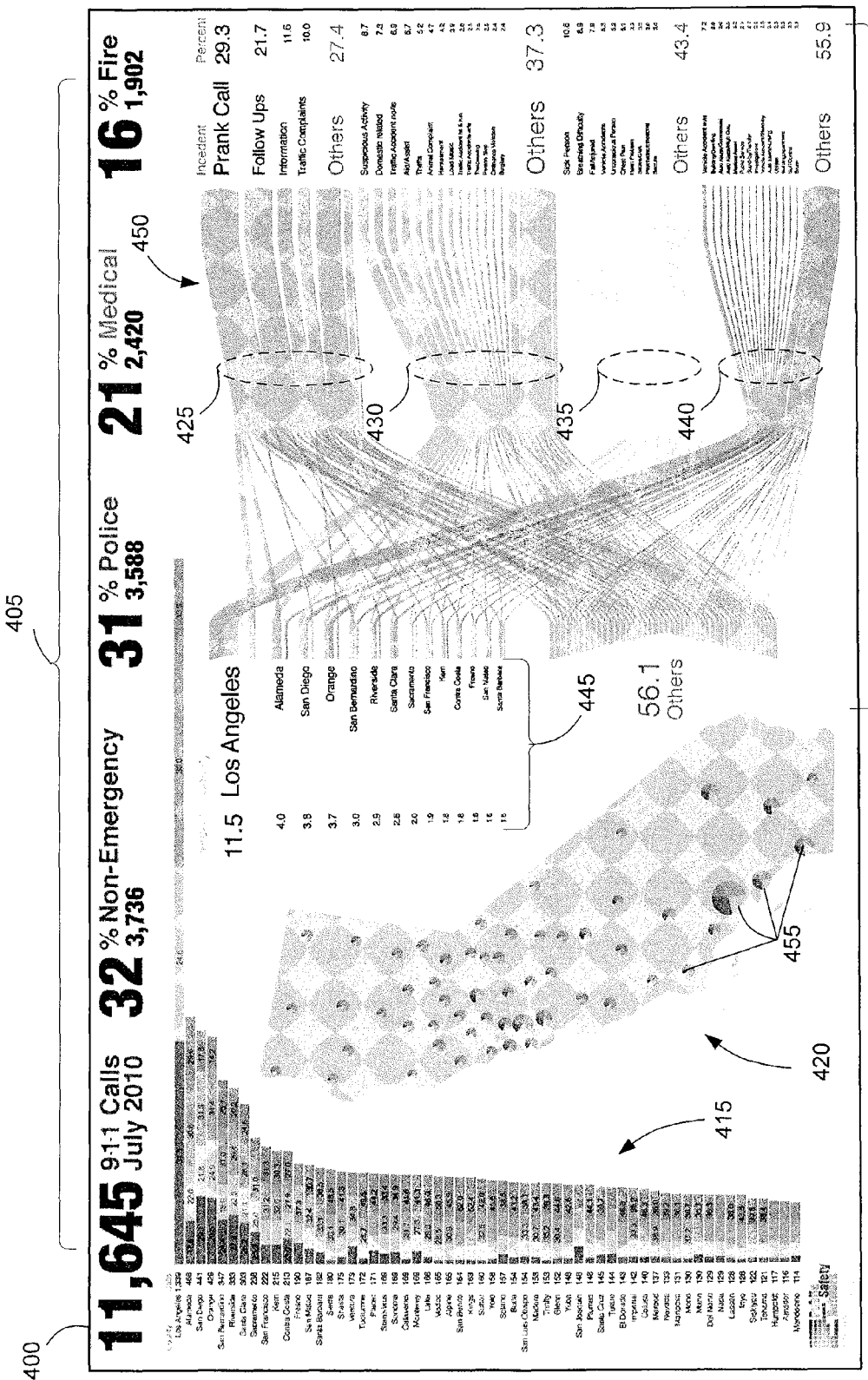

FIG. 4 illustrates a third exemplary dashboard 400 that may be communicated to a browser 120. The dashboard 400 displays call detail and summary statistics as to why people call emergency response centers. The dashboard 400 includes a geographic region 420, a sub region list 415, a status region 405, and a category region 410.

Information in the dashboard 400 may be based on emergency calls generated in a prior month, week, day, or different period. The information is analyzed to categorize the reason behind the emergency call. For example, the emergency calls may be categorized as non-emergency 425, police-related 430, medical-related 435, and fire-related 440. The processor 105 may determine the categories. For example, the processor 105 may determine whether an emergency call is a police-, medical-, or fire-related call by analyzing emergency call information that defines where the emergency call was ultimately routed by the PSAP. In addition, the PSAP receiving the call may specify additional details related to the emergency call, such as whether the call was a prank, traffic-related, etc.

The different categories are represented through various colorized bar graphs, maps and sankey diagrams to give the viewer rapid understanding of the emergency call distributions. That is so that the viewer can quickly understand the types of emergency calls being generated. For example, the color orange may used to represent fire-related calls. Green, blue, and grey may be used to represent medical-, police-, and non-emergency-related calls, respectively.

The status region 405 indicates the percentage of emergency calls that fall into the respective categories. The percentage may be based on emergency calls made throughout the geographic region 420. For example, the percentages may correspond to emergency calls made throughout the state of California.

The category region 410 includes a sankey diagram 450 that matches sub regions 445 of the geographic region 420 to categories. The sankey diagram 450 may be color-coded to enable rapid conveyance of information. The sub regions 445 matched may correspond to a subset of sub regions of the geographic region 420. For example, the sub regions 445 that result in the top ten number of emergency calls may be listed in the category region 410. The sub regions 445 may correspond to the largest municipalities in the geographic region. Other criteria for selecting the sub regions 445 may be used.

Reasons for the emergency calls may be provided for each category. For example, a number of non-emergency calls 425 may correspond to prank calls, follow-up calls, calls for general information, traffic complaints, and the like. Reasons for the police-, medical- and fire-related calls may also be provided. The reasons provided may correspond to those reasons that occur the most frequently.

The sub region list 415 may correspond to a list or a subset list of sub regions of the geographic region. The sub regions listed may correspond to those sub regions that experience the highest number of emergency calls. For each sub region in the sub region list 415, a color-coded bar graph may be provided. The bar graph indicates the percentage of emergency calls within the sub region that fall into the categories described above. The colors in the bar graph may be matched to the colors used in the category region 410 and status region 405 for consistency.

The geographic region 420 may correspond to a state, or a sub region of the state. Alternatively, the geographic region 420 may correspond to an entire country, continent, or other geographic region. One or more charts 455 may be superimposed on the geographic region 420 over sub regions. The charts 455 may correspond to pie charts or other charts that indicate the relative percentage of emergency calls that fall into one category or another. The charts 455 may be color-coded as described above.

Figure 5:
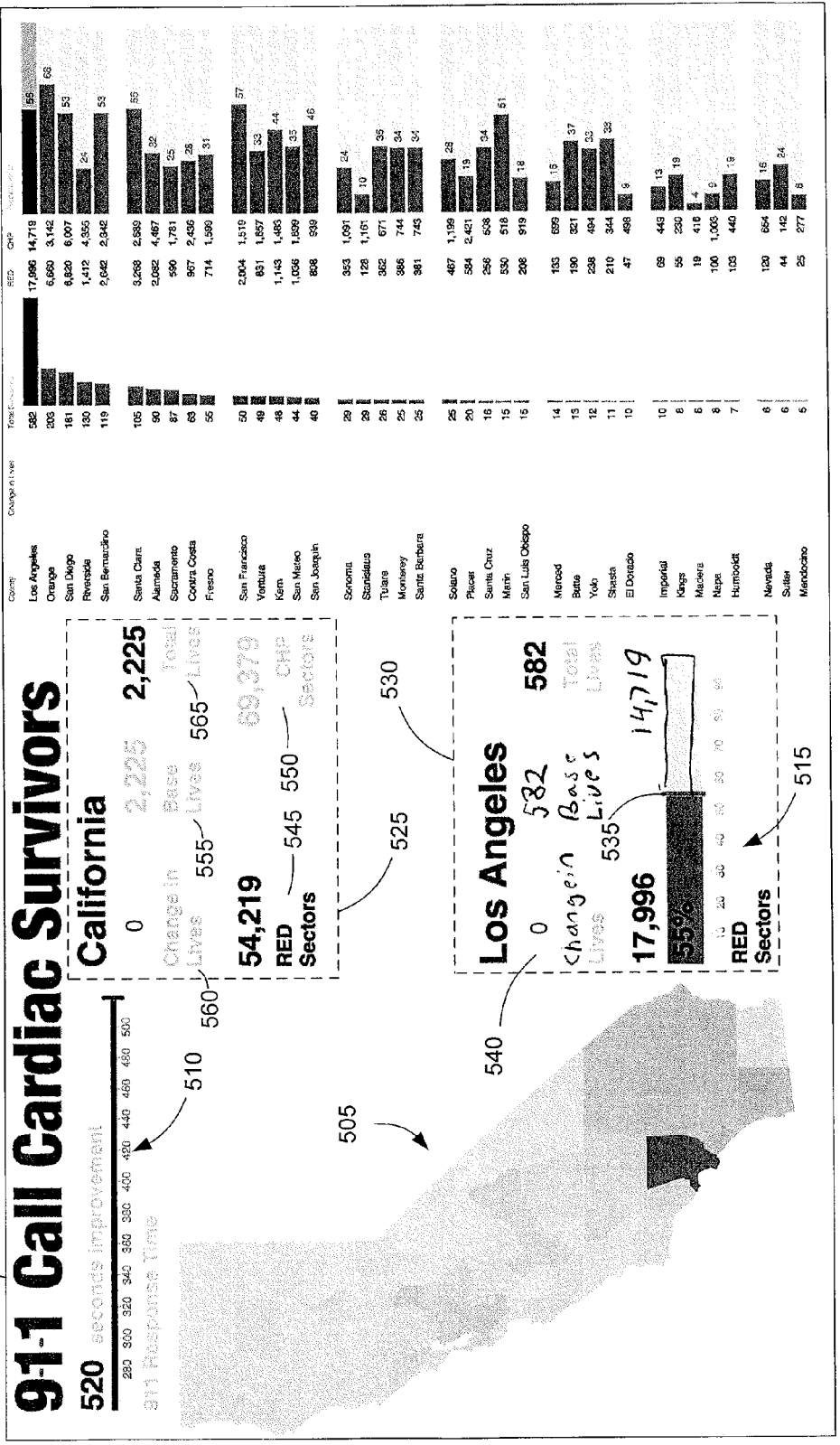
FIG. 5 is an exemplary dashboard that enables predication of a number of survivors of a traumatic medical emergency.

FIG. 5 illustrates a fourth exemplary dashboard 500 that may be communicated to a browser 120 for predicting a survival rate among individuals that experience a life-threatening medical condition where minutes can mean the difference between life and death. The dashboard 500 includes a geographic region 505, a sub region list 520, a geographic region information section 525, a sub region information section 530 that includes a routing control 515, and a response time control 510.

The dashboard 500 is configured to display a prediction of a number of cardiac arrest survivors. However, it is understood that the principals disclosed herein may be applied to predict survival rates associated with other traumatic events. The prediction takes into consideration a number of factors that include the number of incidents (e.g., cardiac arrests) in a geographic region 505, the population of the geographic region 505, and the number of cellular towers in the geographic region 505. For example, the prediction may be calculated according to the following: First, it may be assumed that the number of cardiac arrest cases in a county is approximately 0.096× the county population, that 92% of all cardiac arrest cases result in death, that each one-minute delay in receiving care results in a ten-percentage point decline in likelihood of survival, and that all cardiac arrests result in a 9-1-1 call.

Based on these foregoing assumptions and an iterative Monte Carlo simulation, an estimated average time to administer care is calculated to be 520 seconds with an assumed standard deviation of ±30 seconds.

Given a ratio of RED sectors to non-RED sectors, p, a RED sector delta time, dt, and a total number of calls, n, n*p randomly selected calls are handled by RED sectors and the rest are handled by a state highway patrol. For calls handled by RED sectors, the mean first response time=520−dt and the standard deviation is 30 seconds. Based on the above, the probability of survival may be calculated randomly for each call. Based on this probability, a "crooked" coin is tossed to determine if each call results in a death or not. The number of deaths are tallied up for each sub region for each range of RED sector ratio and RED sector delta time and displayed on the dashboard 500.

The geographic region information section 525 displays the number of RED sectors 545 (i.e., the number of cellular towers routed to primary emergency response centers). Also shown is the number of cellular towers routed to secondary emergency response centers 550 (e.g. California Highway Patrol (CHP) sectors). A base number of lives saved 555, a changed number of lives 560, and a total number of lives save 565 are shown. The total number of lives save 565 is the sum of the base number of lives saved 555 and the changed number of lives 560. As described below, a change in the number of lives saved occurs when a user adjusts either the routing control 515 or the response time control 510, in which case a changed number of lives 560 value is specified.

The sub region information section 530 displays information associated with a sub region selected from the sub region list 520. For example, the city of Los Angeles may be selected in the sub region list 520. In this case, the sub region information section 530 displays a percentage of RED sectors and non-RED sectors (e.g. CHP sectors) in Los Angeles. For example, 55% of the cellular towers in Los Angeles may be RED sectors, and the other 45% may be routed to secondary emergency response centers. A base number of lives saved, total number of lives saves, and a change in the number, of lives saved 540 are also displayed. The respective values correspond to the number of lives saved in the selected sub region based on the current allocation of cellular towers between RED and non-RED sectors. The total number of lives saved is the sum of the base number of lives saved and the change in the number of lives saved 540. As described below, a change in the number of lives saved occurs when a user adjusts either the routing control 515 or the response time control 510, in which case a number appears.

The response time control 510 displays the average amount of time an emergency responder takes to respond to an emergency in the selected sub region. For example, the average response time in Los Angeles may be 520 seconds.

The sub region list 520 lists various sub regions of the geographic region 505. For each sub region in the sub region list 502, a number and graph representing the response time and percentage of RED sectors is provided.

In operation, a user may select a sub region in the sub region list 520. Information associated with the selected sub region is presented in the sub region information section 530. In some implementations, the sub region may be highlighted on the geographic region 505 to enable the user to determine the location of the sub region within the geographic region 505.

The user may then adjust the routing control 515 of the sub region information section 530 to change the allocation of cellular towers between RED and non-RED sectors to predict a number of lives saved if the number or RED sectors is different. For example, the user may slide a selector 535 of the routing control 515 to the left to increase the number of RED sectors. This may result in an increase in the number of lives saved as an increase in the number of RED sectors indicates an increase in the number of emergency calls routed to RED sectors, which are routed to primary emergency response centers. The increase in the number of lives is represented as the number of changed lives 540 shown in the sub region information section 530. The increase is reflected in the total lives saved, which corresponds to the sum of the base number of lives saved and the changed number of lives. Conversely, sliding the selector 535 of the routing control 515 to the right may decrease the number of emergency calls routed to RED sectors. This in turn may decrease the number of lives saved. In this case, the number of changed lives is represented with a negative number.

The user may also adjust a selector of the response time control 510 to predict a number of lives that may be saved if the response to were improved.

The changes in the response time and the percentage of RED sectors is also reflected in the geographic region information section 525 as the change in lives 560, base lives saved 555, and total lives saved 565 correspond to the sum of the change in lives values, base lives save values and total lives saved values associate with the various sub regions.

As shown, the dashboard 500 enables operators to determine hypothetical improvements in the survival rates associated with traumatic medical events, such as cardiac arrests. For example, the operator may adjust the various controls to determine how many additional lives may be saved by configuring emergency calls communicated to cellular towers to be routed to primary emergency response center as opposed to secondary emergency response centers. Based on the information provided, operators may conclude, for example, that it is more cost-effective to reconfigure one or more cellular towers rather than purchase additional emergency equipment, such as ambulances and the like.

Figure 6:
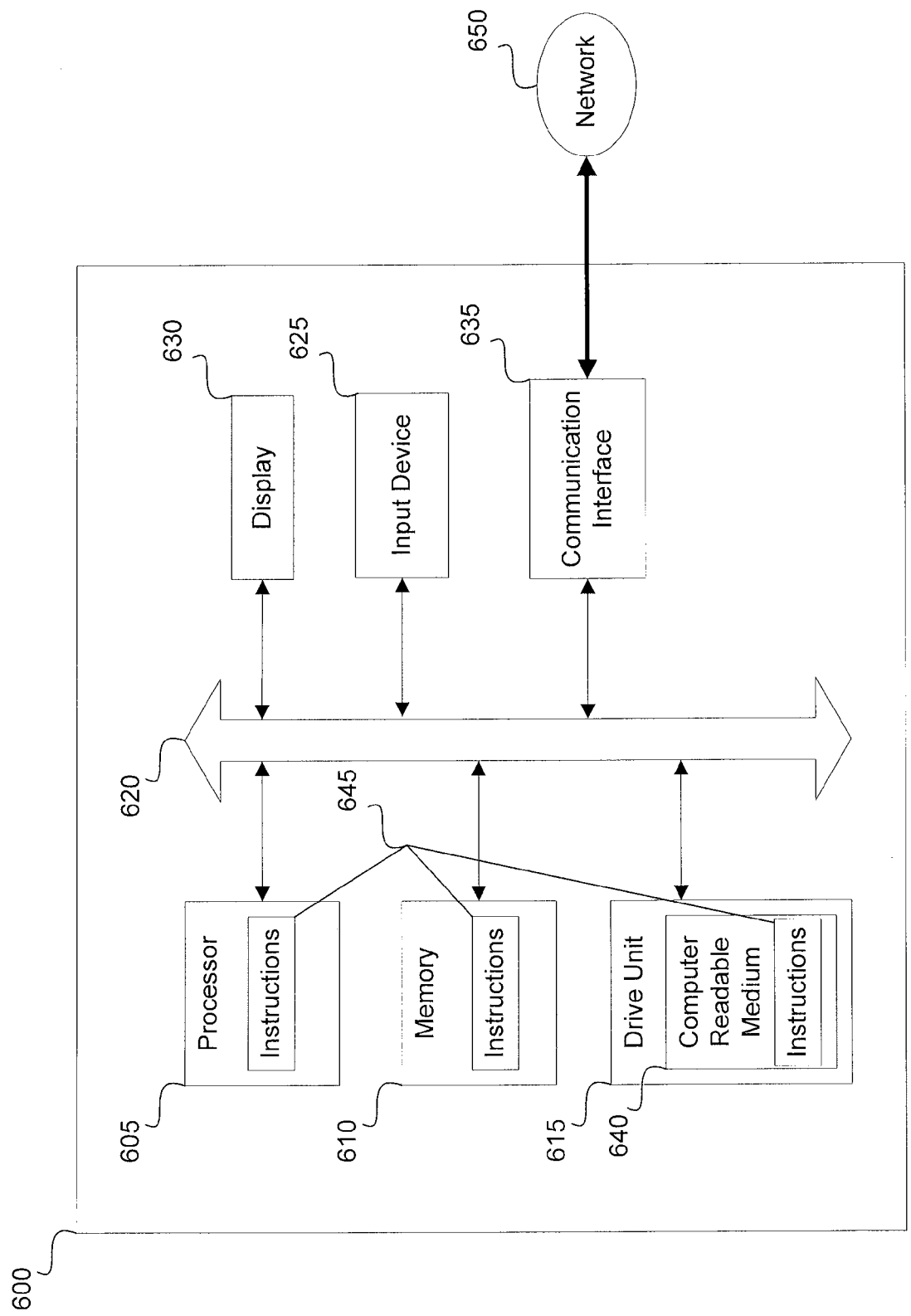
FIG. 6 illustrates a general computer system that may represent any of the computing devices referenced herein.

FIG. 6 illustrates a general computer system 600, which may represent the processor 105, web server 110, or any other computing devices referenced herein. The computer system 600 may include a set of instructions 645 that may be executed to cause the computer system 600 to perform any one or more of the methods or computer-based functions disclosed herein. The computer system 600 may operate as a stand-alone device or may be connected, e.g., using a network, to other computer systems or peripheral devices.

In a networked deployment, the computer system 600 may operate in the capacity of a server or as a client-user computer in a server-client user network environment, or as a peer computer system in a peer-to-peer (or distributed) network environment. The computer system 600 may also be implemented as or incorporated into various devices, such as a personal computer or a mobile device, capable of executing a set of instructions 645 (sequential or otherwise) that specify actions to be taken by that machine. Further, each of the systems described may include any collection of sub-systems that individually or jointly execute a set, or multiple sets, of instructions to perform one or more computer functions.

The computer system 600 may include one or more memory devices 610 on a bus for communicating information, such as the emergency call information database 115 (FIG. 1). In addition, code operable to cause the computer system to perform any of the acts or operations described herein may be stored in the memory 610. The memory 610 may be a random-access memory, read-only memory, programmable memory, hard disk drive or any other type of memory or storage device.

The computer system 600 may include a display 630, such as a liquid crystal display (LCD), a cathode ray tube (CRT), or any other display suitable for conveying information. The display 630 may act as an interface for the user to see the functioning of the processor 605, or specifically as an interface with the software stored in the memory 610 or in the drive unit 615.

Additionally, the computer system 600 may include an input device 625, such as a keyboard or mouse, configured to allow a user to interact with any of the components of system 600.

The computer system 600 may also include a disk or optical drive unit 615, such as the high-latency storage 110 (FIG. 1). The disk drive unit 615 may include a computer-readable medium 640 in which one or more sets of instructions 645, e.g. software, can be embedded. Further, the instructions 645 may perform one or more of the operations as described herein. The instructions 645 may reside completely, or at least partially, within the memory 610 and/or within the processor 605 during execution by the computer system 600. The memory 610 and the processor 605 also may include computer-readable media as discussed above.

The computer system 600 may include a communication interface 635 that enables communications via a network 650. The network 650 may include wired networks, wireless networks, or combinations thereof. The communication interface 635 network may enable communications via any number of communication standards, such as 802.11, 802.12, 802.20, WiMax, cellular telephone standards, or other communication standards.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The method and system may also be embedded in a computer program product, which includes all the features enabling the implementation of the operations described herein and which, when loaded in a computer system, is able to carry out these operations. Computer program in the present context means any expression, in any language, code or notation, of a set of instructions intended to cause a system having an information processing capability to perform a particular function, either directly or after either or both of the following: a) conversion to another language, code or notation; b) reproduction in a different material form.

While the method and system has been described with reference to certain embodiments, it will be understood by those skilled in the art that various changes may be made and equivalents may be substituted without departing from the scope. In addition, many modifications may be made to adapt a particular situation or material to the teachings without departing from its scope. Therefore, it is intended that the present method and system not be limited to the particular embodiment disclosed, but that the method and system include all embodiments falling within the scope of the appended claims.

We claim:

1. A method for predicting a survival rate among individuals, where the survival rate depends in part on a responsiveness of emergency personnel, and the responsiveness of the emergency personnel depends in part on an amount of time taken to route an emergency call to a primary emergency response center, the method comprising:
   determining, by a computer system, a quantity of emergency calls initially routed to a primary emergency response center;
   determining, by the computer system, a quantity of emergency calls initially routed to a secondary emergency response center that, in turn, routes the emergency calls to the primary emergency response center;
   calculating, by the computer system, a survival rate amount individuals according to a function of the determined quantity of the number of emergency calls initially routed to a primary emergency response center and the quantity of emergency calls initially routed to a secondary emergency response center;
   displaying the calculated survival rate on a terminal;
   displaying a number indicative of a quantity of emergency calls routed to a primary emergency response center; and
   displaying a field that facilitates specifying a different quantity of emergency calls routed to a primary emergency response center to facilitate recalculation of the survival rate based on the specified quantity.

2. The method according to claim 1, wherein the emergency calls initially routed to a secondary emergency response center correspond to cellular telephone calls.

3. The method according to claim 2, wherein a cell tower through which the cellular telephone communicates is configured to route all emergency calls to the secondary emergency response center.

4. The method according to claim 1, further comprising generating, by a computer server, browser code executable by a browser to cause the browser to display the calculated survival rate.

5. The method according to claim 4, wherein the browser code is executable to display a geographic image that represents one or more geographic regions within a state, wherein each of the one or more geographic regions is selectable to enable calculating a survival rate associated with the selected one or more geographic regions.

6. The method according to claim 4, wherein the browser code is executable to display the quantity of emergency calls routed to a primary emergency response center, and to display the field that facilitates specifying the different quantity of emergency calls routed to the primary emergency response center.

7. The method according to claim 4, wherein the browser code is executable to display an average response time associated with the calculated survival rate, and to display a field that enables specifying a different average response time to enable recalculation of the survival rate based on the specified response time.

8. A system for predicting a survival rate among individuals, where the survival rate depends in part on a responsiveness of emergency personnel, and the responsiveness of the emergency personnel depends in part on an amount of time taken to route an emergency call to a primary emergency response center, the system comprising:
   a computer system configured to determine a number of emergency calls initially routed to a primary emergency response center and a number of emergency calls initially routed to a secondary emergency response center that, in turn, routes the emergency calls to the primary emergency response center, and calculate a survival rate amount individuals according to a function of the determined number of the number of emergency calls initially routed to a primary emergency response center and the number of emergency calls initially routed to a secondary emergency response center; and
   a server configured to generate browser code executable by a browser to cause the browser to display:
   the calculated survival rate on a terminal
   a number indicative of a quantity of emergency calls routed to a primary emergency response center; and
   a field that facilitates specifying a different quantity of emergency calls routed to a primary emergency response center to facilitate recalculation of the survival rate based on the specified quantity.

9. The system according to claim 8, wherein the emergency calls initially routed to a secondary emergency response center correspond to cellular telephone calls.

10. The system according to claim 8, wherein a cell tower through which the cellular telephone communicates is configured to route all emergency calls to the secondary emergency response center.

11. The system according to claim 8, wherein the browser code is executable to display a geographic image that represents one or more geographic regions within a state, wherein each of the one or more geographic regions is selectable to enable calculating a survival rate associated with the selected one or more geographic regions.

12. The system according to claim 8, wherein the browser code is executable to display the quantity of emergency calls routed to a primary emergency response center, and to display the field that facilitates specifying the different quantity of emergency calls routed to the primary emergency response center.

13. The system according to claim 8, wherein the browser code is executable to display an average response time associated with the calculated survival rate, and to display a field that enables specifying a different average response time to enable recalculation of the survival rate based on the specified response time.

14. A non-transitory machine-readable storage medium having stored thereon a computer program comprising at least one code section for predicting a survival rate among individuals, where the survival rate depends in part on a responsiveness of emergency personnel and the responsiveness of the emergency personnel depends in part on an amount of time taken to route an emergency call to a primary emergency response center, the at least one code section being executable by a machine for causing the machine to perform acts of:
   determining a number of emergency calls initially routed to a primary emergency response center;
   determining a number of emergency calls initially routed to a secondary emergency response center that, in turn, routes the emergency calls to the primary emergency response center;
   calculating a survival rate amount individuals according to a function of the determined number of the number of emergency calls initially routed to a primary emergency response center and the number of emergency calls initially routed to a secondary emergency response center;
   displaying the calculated survival rate on a terminal;
   displaying a number indicative of a quantity of emergency calls routed to a primary emergency response center; and
   displaying a field that facilitates specifying a different quantity of emergency calls routed to a primary emergency response center to facilitate recalculation of the survival rate based on the specified quantity.

15. The non-transitory machine-readable storage medium according to claim 14, wherein the number of emergency calls initially routed to a secondary emergency response center correspond cellular telephone calls.

16. The non-transitory machine-readable storage medium according to claim 14, wherein a cell tower through which the cellular telephone communicates is configured to route all emergency calls to the secondary emergency response center.

17. The non-transitory machine-readable storage medium according to claim 14, wherein the at least one code section is further executable by the machine for causing the machine to perform acts of: generating browser code executable by a browser to cause the browser to display the calculated survival rate.

18. The non-transitory machine-readable storage medium according to claim 17, wherein the browser code is executable to display a geographic image that represents one or more geographic regions within a state, wherein each of the one or more geographic regions is selectable to enable calculating a survival rate associated with the selected one or more geographic regions.

19. The non-transitory machine-readable storage medium according to claim 17, wherein the browser code is executable to display the quantity of emergency calls routed to the primary emergency response center, and to display the field that facilitates specifying the different quantity of emergency calls routed to the primary emergency response center.

20. The non-transitory machine-readable storage medium according to claim 17, wherein the browser code is executable to display an average response time associated with the calculated of the survival rate, and to display a field that enables specifying a different average response time to enable recalculation of the survival rate based on the specified response time.

* * * * *